United States Patent
Vo-Dinh et al.

(10) Patent No.: US 6,744,503 B2
(45) Date of Patent: Jun. 1, 2004

(54) MONITORING OF VAPOR PHASE POLYCYCLIC AROMATIC HYDROCARBONS

(75) Inventors: Tuan Vo-Dinh, Knoxville, TN (US); Mohammad R. Hajaligol, Midlothian, VA (US)

(73) Assignee: Philip Morris Incorporated, New York, NY (US)

(*) Notice: Subject to any disclaimer, the term of this patent is extended or adjusted under 35 U.S.C. 154(b) by 159 days.

(21) Appl. No.: 10/022,239

(22) Filed: Dec. 20, 2001

(65) Prior Publication Data

US 2003/0117619 A1 Jun. 26, 2003

(51) Int. Cl.$^7$ ............................. G01J 3/30; G01N 21/64
(52) U.S. Cl. .................... 356/318; 356/317; 250/458.1; 250/459.1
(58) Field of Search ................................ 356/317–318, 356/326, 331; 250/458.1, 459.1, 461.2

(56) References Cited

U.S. PATENT DOCUMENTS

| | | | |
|---|---|---|---|
| 3,749,495 A | | 7/1973 | Wilkins et al. |
| 3,788,752 A | | 1/1974 | Slavin et al. |
| 3,975,098 A | | 8/1976 | West |
| 4,432,225 A | * | 2/1984 | Hayes et al. ............. 250/458.1 |
| 4,569,592 A | * | 2/1986 | Osada et al. ................ 356/318 |
| 4,577,109 A | * | 3/1986 | Hirschfeld ............... 250/461.1 |
| 4,679,939 A | | 7/1987 | Curry et al. |
| RE32,598 E | | 2/1988 | White |
| 5,220,172 A | * | 6/1993 | Berthold et al. ......... 250/461.1 |
| 5,477,218 A | | 12/1995 | Manmoto et al. |
| 5,684,580 A | * | 11/1997 | Cooper et al. .............. 356/301 |
| 5,748,311 A | | 5/1998 | Hamann et al. |
| 5,793,478 A | | 8/1998 | Rader et al. |
| 5,880,830 A | | 3/1999 | Schechter |
| 5,993,194 A | | 11/1999 | Lemelson et al. |
| 6,008,894 A | * | 12/1999 | Schmucker et al. ........ 356/318 |
| 6,008,895 A | * | 12/1999 | Wahl et al. ................. 356/311 |
| 6,091,843 A | | 7/2000 | Horesh et al. |
| 6,576,911 B1 | * | 6/2003 | Potyrailo et al. ........ 250/458.1 |

OTHER PUBLICATIONS

J.P. Alarie et al. "A Fiber–Optic Cyclodextrin–Based Sensor", Talanta, vol. 38, No. 5, pp. 529–534, 1991, printed in Great Britain.

Tuan Vo–Dinh, "Fluorescence Line–Narrowing Spectrometry of Polycyclic Compounds on Filter Paper Substrates", American Chemical Society, Analytical Chemistry, vol. 58, No. 14, Dec. 1986, pp. 3135–3139.

Tuan Vo–Dinh et al., "Laser–Induced Room–Temperature Phosphorescence Detection of Benzo[a]pyrene–DNA Adducts", American Chemical Society, Analytical Chemistry, vol. 59, No. 8, Apr. 15, 1987, pp. 1093–1095.

(List continued on next page.)

*Primary Examiner*—F. L. Evans
*Assistant Examiner*—Kara Geisel
(74) *Attorney, Agent, or Firm*—Burns, Doane, Swecker & Mathis, LLP

(57) ABSTRACT

An apparatus for monitoring vapor phase polycyclic aromatic hydrocarbons in a high-temperature environment has an excitation source producing electromagnetic radiation, an optical path having an optical probe optically communicating the electromagnetic radiation received at a proximal end to a distal end, a spectrometer or polychromator, a detector, and a positioner coupled to the first optical path. The positioner can slidably move the distal end of the optical probe to maintain the distal end position with respect to an area of a material undergoing combustion. The emitted wavelength can be directed to a detector in a single optical probe 180° backscattered configuration, in a dual optical probe 180° backscattered configuration or in a dual optical probe 90° side scattered configuration. The apparatus can be used to monitor an emitted wavelength of energy from a polycyclic aromatic hydrocarbon as it fluoresces in a high temperature environment.

39 Claims, 5 Drawing Sheets

OTHER PUBLICATIONS

Christopher L. Stevenson et al., "Analysis of Polynuclear Aromatic Compounds Using Laser–Excited Synchronous Fluorescence", Analytica Chimica Acta, 303 (1995), pp. 247–253.

Christopher L. Stevenson et al., "Laser–Excited Synchronous Luminescence Spectroscopy", Applied Spectroscopy, vol. 47, No. 4, 1993, pp. 430–435.

T. Vo–Dinh et al., "Screening Polynuclear Aromatic Pollutants in Ambient and Indoor Air by Synchronous Luminescence", 79th Annual Meeting of the Air Pollution Control Association Minneapolis, Minnesota, Jun. 22–27, 1986, 86–32.2, pp. 1–8.

Tuan Vo–Dinh, "Significance of Chemical Analysis of Polycyclic Aromatic Compounds and Related Biological Systems", Chemical Analysis of Polycyclic Aromatic Compounds, 1989, pp. 1–30.

A.D. Campiglia et al., "Fiber Optic Sensor for Laser–Induced Room–Temperature Phosphorescence Detection of Polycyclic Aromatic Compounds", Talanta 43 (1996), pp 1805–1814, The International Journal of Pure and Applied Analytical Chemistry, Amsterdam, The Netherlands.

Tuan Vo–Dinh, "Development of a Dosimeter for Personnel Exposure to Vapors of Polyaromatic Pollutants", Environmental Science & Technology, vol. 19, No. 10, pp. 997–1003, Oct. 1985.

T. Vo–Dinh et al., "Detection of Polyaromatic Compounds Using Antibody–Based Fiberoptics Fluoroimmunosensors", Polynuclear Aromatic Hydrocarbons: Measurements, Means, and Metabolism, Battelle Press, International Symposium on Polynuclear Aromatic Hydrocarbons, Gaithersburg, MD, 1987, pp. 965–979.

T. Vo–Dinh et al., Screening Air Samples for Polynuclear Aromatic Compounds: A Field Study, Specialty Conference on Measurement and Monitoring of Non–Criteria (Toxic) Contaminants, Air Pollution Control Assoc., Chicago IL, Mar. 23–4, 1983, 12 pages.

R. P. Cooney et al., "The Sit Image Vidicon as a Gas–Phase Fluorescence Detector for Gas Chromatography", Analytica Chimica Acta 89 (1977), pp. 9–19.

T. Vo–Dinh et al., "Immunosensors: Principles and Applications", Immunomethods 3, pp. 85–92 (1993).

Brian M. Cullum et al., "High–Temperature Fluorescence Measurements and Instrumentation for Polyaromatic Hydrocarbons (PAH): A Review", Journal of Polycyclic Aromatic Compounds, vol. 18, No. 1, pp. 25–47 (2000).

Zhenhuan Chi et al., "Laser–Induced Fluorescence Studies of Polycyclic Aromatic Hydrocarbons (PAH) Vapors at High Temperatures", Spectrochimica Acta, Part A, vol. 57, pp. 1377–1384 (2001).

J. C. Andrea et al., "Applications of Fast Fourier Transform to Deconvolution in Single Photon Counting", J. Phys Chem., vol. 83, p. 2285 (1979).

* cited by examiner

US 6,744,503 B2

MONITORING OF VAPOR PHASE POLYCYCLIC AROMATIC HYDROCARBONS

STATEMENT REGRADING FEDERALLY SPONSORED RESEARCH OR DEVELOPMENT

The United States Government has rights in this invention pursuant to Contract No. DE-AC05-00OR22727 between the United States Department of Energy and Martin Marietta Energy Systems, Inc.

BACKGROUND

1. Field of the Invention

The present invention is directed to an instrument that monitors the composition of a vapor. More specifically, the present invention is directed to an instrument that in situ monitors for vapor phase polycyclic aromatic hydrocarbons in a burning cigarette.

2. Background Information

In the description of the background of the present invention that follows reference is made to certain structures and methods, however, such references should not necessarily be construed as an admission that these structures and methods qualify as prior art under the applicable statutory provisions. Applicants reserve the right to demonstrate that any of the referenced subject matter does not constitute prior art with regard to the present invention.

Polyaromatic hydrocarbons (PAHs) are a large class of multi-ring structures that contain carbon and hydrogen atoms. These compounds are environmentally and biologically important and originate from a wide variety of natural and anthropogenic sources. For example, a PAH can be generated by the incomplete combustion or pyrolysis of organic matter. Several of the more prevalent formation sources for PAHs include combustion, catalytic cracking of petroleum products and coal coking. Each of these processes occurs at various temperatures and under various environmental conditions, therefore leading to the formation of different PAHs.

Extensive research in the field of high-temperature fluorescence measurements of PAHs has occurred in the field of combustion analysis. Due to the great number of applications of combustion in our daily lives (e.g., heating, cooking, cigarette smoking, and so forth), PAHs are formed in great abundance in fuel rich combustion environments. These fuel rich environments can allow the PAH to escape further combustion and thus be released. Emitted PAHs generally adsorb on the surface of soot particles, thus allowing the dispersion of these compounds throughout the environment. Through the use of techniques such as fluorescence spectroscopy and hyperspectral fluorescence imaging, these species can be monitored during simple, controlled combustion reactions. However, due to the difficulties associated with identification of a specific species (because of spectral shifts, line broadening and spectral overlap), high-temperature fluorescence measurements are often used to provide a qualitative proof of the general presence of PAHs but not in the identification of the specific species being measured.

Several procedures are known for obtaining compound specific information for evaluation of PAH contamination. However, additional sample preparation steps of collection and extraction make real time or in-situ measurements impossible. For example, gas chromatography/mass spectrometry (GCMS) has previously been used to detect the presence of PAHs. Analysis of PAHs by GCMS requires the prior collection of suspected PAH containing material and extraction of the PAH with solvents (such as methanol). Additionally, GCMS methods, in particular, are complicated, time consuming, and expensive, requiring significant resources such as high-vacuum equipment and extensive investment in highly trained personnel. Further, it is not cost-effective to apply previous PAH analysis techniques routinely to samples that may not, in fact, contain any relevant levels of PAH. Moreover, GCMS methods and similar techniques are not adaptable to in-situ environments in which vapor-phase analysis is to be conducted nor can GCMS be used for fast feedback which can be required for both environmental protection and for industrial process control.

Common forms of real-time analysis procedures utilize optical spectroscopy and, more particularly, fluorescence analysis. This is due to the inherent sensitivity of the technique and the great number of methods that have been developed over the years for differentiation of fluorescence signals from the intense background emissions often present at high temperatures. Other techniques include time-resolved fluorescence and hyperspectral fluorescence imaging. A more complete treatment of known methods in PAH analysis can be found in Brian M. Cullum et al., *High-Temperature Fluorescence Measurements and Instrumentation for Polyaromatic Hydrocarbons (PAH): A Review*, Journal of Polycyclic Aromatic Compounds, Vol. 18, No. 1, p. 25 (2000), the entire contents of which are herein incorporated by reference.

Although several procedures are available to analyze PAHs, the ability to provide in situ analysis of a PAH in the vapor phase is very limited. For example, U.S. Pat. No. 5,880,830, discloses a method to detect PAHs. The method analyzes aerosols by depositing particles on a substrate or filter and subsequently using ultraviolet light spectroscopy methods to detect the presence of a PAH.

In evaluating PAHs in combustion environments, it would be desirable to monitor the combustion products for PAH content in real time and in situ. For example, in the evaluation of burning cigarettes, PAHs, which have a very low volatility, are generally combined with smoke particles (TPMs). The analysis of these products requires the chemical analysis of TPM which is lengthy and tedious. In addition, locating regions in a cigarette where PAH production occurs is currently not practical but could be of interest in product development. However, in-situ monitoring inside a combusting material is difficult because the temperatures encountered in burning environments, such as a cigarette, can be on the order of about 500° C. or higher.

The monitoring and chemical analysis of PAHs is of interest to both environmental and toxicological scientists and the real-time detection and characterization of PAHs, including PAHs in vapor phases, during the combustion processes, such as the combustion of tobacco, would be desirable to facilitate a better understanding of the smoke formation process and the development of new products with less PAH production.

SUMMARY OF THE INVENTION

A monitoring apparatus for one or more vapor phase polycyclic aromatic hydrocarbons (PAHs) in a high-temperature environment has an excitation source producing electromagnetic radiation, an optical path having at least a first optical probe that optically communicates the electromagnetic radiation received at a proximal end to a distal end such that the electromagnetic radiation interacts with at least one vapor phase polycyclic aromatic hydrocarbon produced by a material undergoing combustion and produces at least one emitted wavelength of radiation characteristic of the at least one vapor phase polycyclic aromatic hydrocarbon. A positioner is coupled to the optical path and can slidably move the distal end of the first optical probe to maintain the distal end position at a desired position with respect to an area of the material undergoing combustion. In a single optical probe 180° backscattered configuration, the first optical probe receives the radiation at at least one emitted wavelength at the distal end and optically communicates the radiation from the distal end of the first optical probe to the proximal end thereof such that the wavelength of radiation is received by a wavelength separator in optical communication therewith and operatively connected to a detector. The optical path can have an optional second optical probe and can be arranged in a dual optical probe 180° backscattered configuration or in a dual optical probe 90° side scattered configuration and in which the second optical probe receives the radiation at at least one emitted wavelength emitted from the vapor phase PAH and directs the radiation to a wavelength separator operatively connected to a detector. The wavelength separator can be a spectrometer or a monochromator and optional time-resolved detection capability can be provided by a trigger system.

In an additional embodiment, a vapor phase polycyclic aromatic hydrocarbon monitoring apparatus comprises means for generating electromagnetic radiation, means for directing the electromagnetic radiation to a gaseous by-product produced by a material undergoing combustion, and means for receiving emitted radiation from the material undergoing combustion having at least one wavelength characteristic of a polycyclic aromatic hydrocarbon and directing the emitted radiation to a detecting means. The means for directing the electromagnetic radiation and/or the means for receiving the emitted radiation is positionable to be co-located with the sample. The monitoring apparatus can further comprise a means for analyzing the emitted radiation from the material undergoing combustion and a means for time resolving the monitoring apparatus.

A method of monitoring at least one vapor phase PAH by detecting electromagnetic radiation is provided having the steps of producing electromagnetic radiation, directing the electromagnetic radiation along a first optical probe, positioning a distal end of the first optical probe with respect to an area containing gaseous by-products of a material undergoing combustion, interacting at least a portion of the produced electromagnetic radiation with the gaseous by-products to produce emitted radiation characteristic of at least one PAH, and monitoring the emitted radiation. Monitoring can be directing the emitted radiation to a wavelength separator using either the first optical probe or a second optical probe. The positioning locates the distal end of the first optical probe substantially co-located outside an area of the material undergoing combustion, within a combustion zone of a material undergoing combustion, or within an area of the material undergoing combustion outside the combustion zone and detecting a vapor phase polycyclic aromatic hydrocarbon.

BRIEF DESCRIPTION OF THE DRAWING FIGURES

Features of the invention will become apparent from the following detailed description of preferred embodiments in connection with the accompanying drawings in which like numerals designate like elements and in which.

DETAILED DESCRIPTION OF THE PREFERRED EMBODIMENTS

Figure 1:
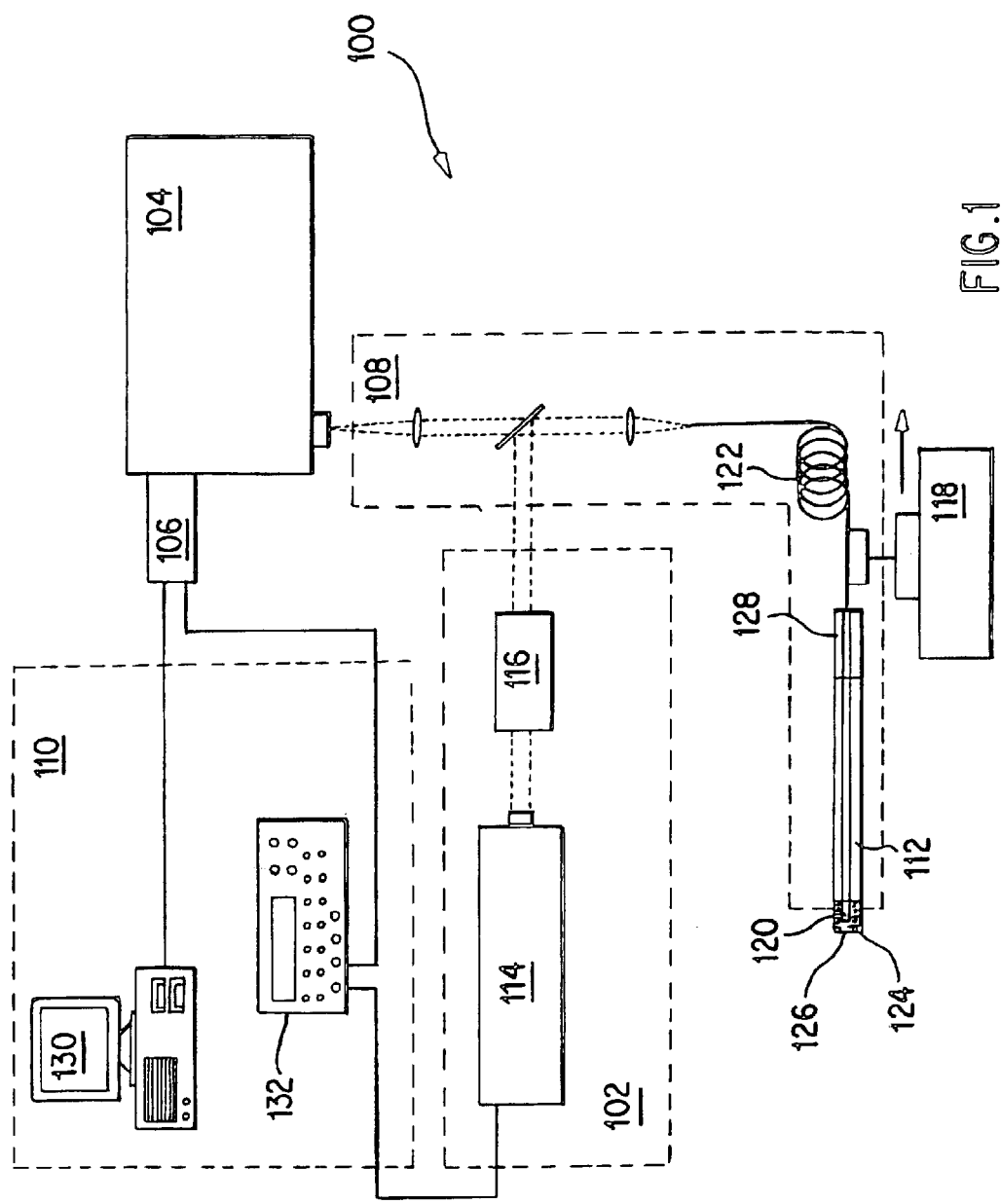
FIG. 1 is an illustration of an embodiment of a PAH monitoring apparatus.

FIG. 1 is a schematic diagram of an embodiment of an apparatus 100 for monitoring one or more vapor phase polycyclic aromatic hydrocarbons (PAHs) in a high-temperature environment (e.g., T≧200° C.). The apparatus 100 has an excitation source 102, a wavelength separator 104 coupled with a detector 106, and an optical path 108. A controller 110 interfaces with the excitation source 102 to produce electromagnetic radiation to probe a vapor sample from a source 112, such as a burning cigarette, and with the detector 106. Fluorescence at at least one wavelength emitted from the vapor sample 112 is collected by the wavelength separator 104 and the detector 106. The electromagnetic radiation can occur at a single wavelength or a plurality of wavelengths.

In the embodiment shown in FIG. 1, the excitation source 102 is a pump laser 114 coupled with a dye unit 116. Alternatively, the excitation source 102 can be any suitable laser or any suitable light source and is preferably tunable. For example, the excitation source 102 can be pump laser coupled with an all solid-state tunable source, such as an optical parametric oscillator (OPO), or the excitation source 102 can be a nitrogen laser. When using a nitrogen laser, the optical path 108 includes a bandpass filter (not shown) to remove plasma emission lines from the excitation source and to produce a desired emission line for use as the fluorescence probe. An exemplary emission line from a nitrogen laser is the 337 nm emission line.

Figure 2:
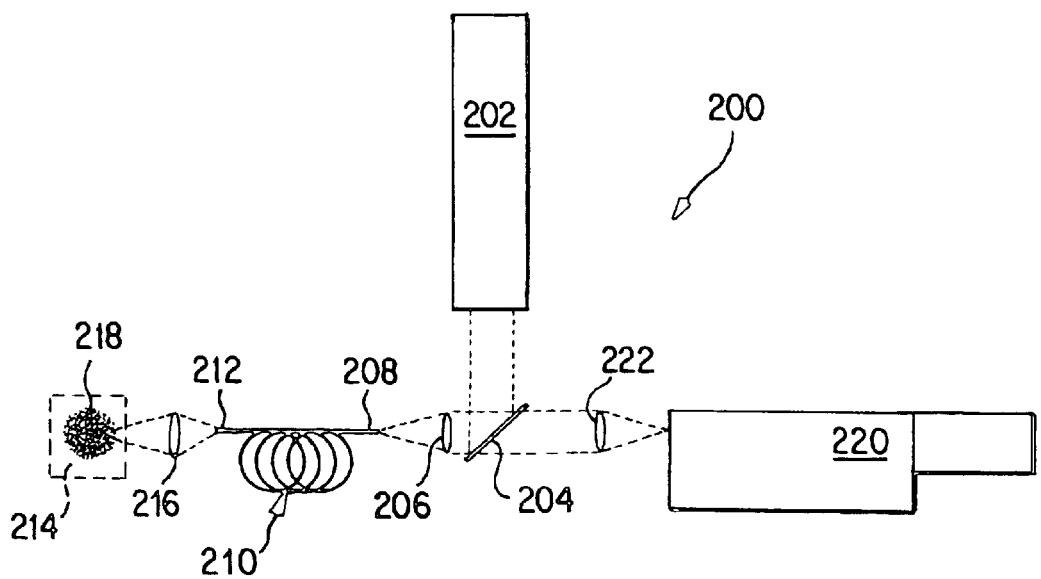
FIG. 2 is an embodiment of an optical path in a single optical probe 180° backscattered configuration.

FIG. 2 shows one embodiment of an optical path 200 for a PAH monitoring apparatus. This embodiment represents a single optical probe 180° backscattered configuration. Radiation generated from the excitation source 202 is split into reference path radiation and incident path radiation by a splitting means 204, such as, for example, a dichroic mirror. The incident path radiation is manipulated by a first optically significant surface 206, such as a lens, and received by the proximal end 208 of an optical probe 210. The optical probe 210 conveys the incident path radiation along its length, which can be a tortuous path, to a distal end 212 from which the incident path radiation projects to an interaction area 214. The incident path radiation can optionally be optically manipulated after the optical probe 210 and prior to the interaction area 214 by a second optically significant surface 216, such as a lens. At least a portion of the incident path radiation interacts with the vapor sample from a source 218 within the interaction area 214 and stimulates fluorescence emission which is collected by the distal end 212 and returns via the optical probe 210 to the wavelength separator 220. An optional optically significant surface 222 can be placed in the optical path 200 and can optically manipulate the reference path and/or the emitted fluorescence prior to entering the wavelength separator 220.

For purposes of illustration, the optical path shown in FIG. 2 can be incorporated in the FIG. 1 embodiment. However, the FIG. 1 embodiment of a PAH monitoring apparatus can be implemented in ways other than the manner illustrated and can incorporate other optical path arrangements than the embodiment shown in FIG. 2.

Figure 3:
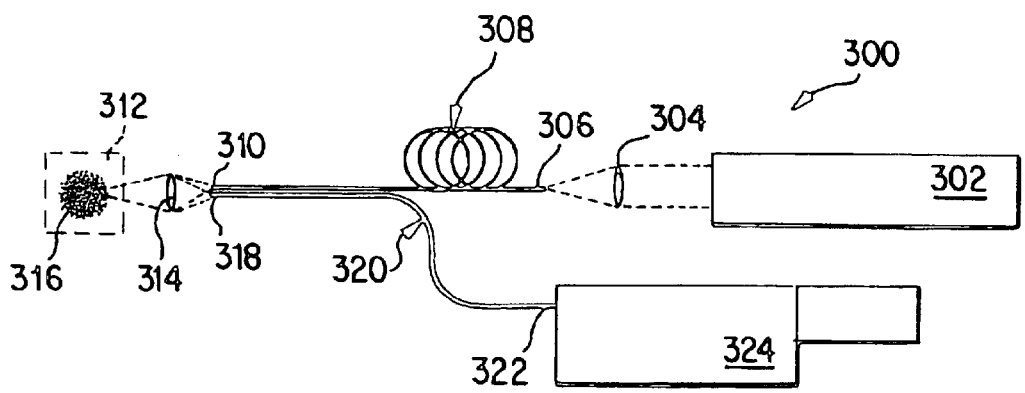
FIG. 3 is an embodiment of an optical path in a dual optical probe 180° backscattered configuration.

FIG. 3 shows a second embodiment of an optical path 300 for a PAH monitoring apparatus. This embodiment represents a dual optical probe 180° (angle θ) backscattered configuration. Note that the angle θ may be different than 180° (e.g., 120°, 150°, etc . . . ). Radiation generated from the excitation source 302 (alternatively called incident path radiation in this embodiment) is manipulated by a first optically significant surface 304, such as a lens, and received by the proximal end 306 of a first optical probe 308. The first optical probe 308 conveys the incident path radiation along its length, which can be a tortuous path, to a distal end 310 from which the incident path radiation projects to an interaction area 312. The incident path radiation can optionally be optically manipulated after the first optical probe 308 and prior to the interaction area 312 by a second optically significant surface 314, such as a lens. Incident path radiation interacts with the vapor sample from source 316 within the interaction area 312 and stimulates fluorescence emission which is collected by the distal end 318 of a second optical probe 320 substantially collocated with the distal end 310 of the first optical probe 308. Hence, the distal end 318 of a second optical probe 320 is oriented to receive emitted fluorescence radiation that is projected approximately 180° from the angle of incidence of the incident path radiation. The second optical probe 320 conveys the emitted fluorescence radiation along its length, which can be a tortuous path, to a proximal end 322 from which the emitted fluorescence radiation projects to the wavelength separator 324.

Figure 4:
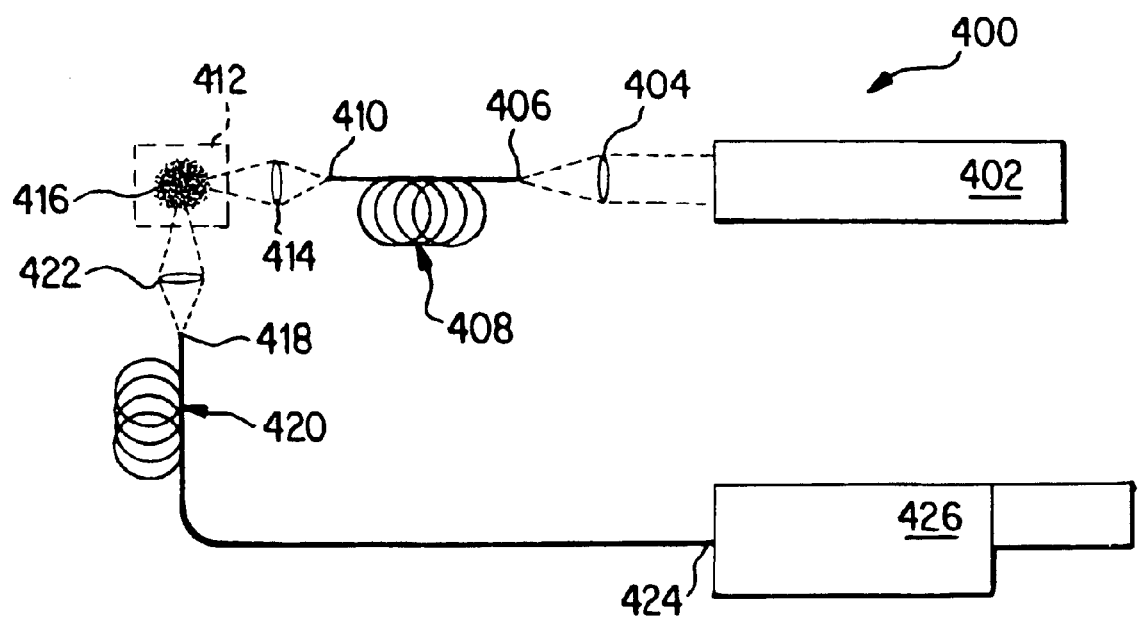
FIG. 4 is an embodiment of an optical path in a dual optical probe 90° side scattered configuration.

FIG. 4 shows another embodiment of an optical path 400 for a PAH monitoring apparatus. This embodiment represents a dual optical probe 90° (angle θ) side scattered configuration. Note that the angle θ may be different than 90° (e.g., 30°, 60°, etc . . . ). Radiation generated from the excitation source 402 (alternatively called incident path radiation in this embodiment) is manipulated by a first optically significant surface 404, such as a lens, and received by the proximal end 406 of a first optical probe 408. The first optical probe 408 conveys the incident path radiation along its length, which can be a tortuous path, to a distal end 410 from which the incident path radiation projects to an interaction area 412. The incident path radiation can optionally be optically manipulated after the first optical probe 408 and prior to the interaction area 412 by a second optically significant surface 414, such as a lens. Incident path radiation interacts with the vapor sample from source 416 within the interaction area 412 and stimulates fluorescence emission which is collected by the distal end 418 of a second optical probe 420 after being manipulated by a third optically significant surface 422, such as a lens. The distal end 418 is located substantially perpendicular to the angle of incidence of the incident path radiation with the vapor sample. The second optical probe 420 conveys the emitted fluorescence radiation along its length, which can be a tortuous path, to a proximal end 424 from which the emitted fluorescence radiation projects to the wavelength separator 426.

Because there are two probes in the configurations in FIGS. 3 and 4, splitting of the generated radiation from the excitation source can be by use of a dichroic mirror placed in the optical path similar to FIG. 2 or by coatings or split lens systems, such as mangin mirrors, or the like.

The fluorescence emissions from vapor phase PAHs can be directed by the optical path to be incident on a wavelength separator. In one aspect, the wavelength separator can be a spectrometer that combines the emitted fluorescence wavelengths from the vapor sample and the reference path radiation using a beam combiner and projects the combined beam on a grating at an angle of incidence by which the combined beam is spread across the detector surface. A suitable spectrometer is a Triax-190 ISA spectrometer with a 600-groove per mm grating for spectral dispersion available from Triax of Edison, N.J. The Triax-190 spectrometer has a spectral resolution of approximately 0.8 nm for an entrance slit of 100 microns. In another aspect, the wavelength separator can be a monochromator that receives incident radiation and achieves a monochromatic radiation (radiation within a frequency bandwidth) output to a detector. A suitable monochromator is Model H10V available from Jobin Yvon/Horiba of Edison N.J.

A fluorescence signal can be detected by any suitable detector, such as an intensified charge-coupled device (CCD), available from Roper Scientific of Trenton, N.J. As shown in FIG. 1, the detector 106 is interfaced to a controller 110, which can comprise a computer 130 for data collection and processing.

In one aspect and as depicted in the exemplary embodiment of FIG. 1, the vapor sample can be a gaseous phase of combusted material (e.g., smoke from a burning cigarette) and the distal end of the optical probe can be substantially co-located with an area of the material undergoing combustion or proximate a high-temperature zone of a gaseous environment to excite and collect the fluorescence from a PAH. The optical probe can be located such that the distal end thereof is substantially co-located outside an area of the material undergoing combustion, within a combustion zone of a material undergoing combustion, or within an area of the material undergoing combustion outside the combustion zone. Alternatively, the sample can be a gaseous phase of a high-temperature exhaust gas environment such as exhaust from a combustion engine or a gas turbine engine, effluent at elevated temperatures such as emissions from power generating plants, or the like.

Further, the optical probe can be comprised of a single optical fiber or a plurality of optical fibers that can propagate an optical signal (e.g., a specific wavelength or a range of specific wavelengths) from a first end to a second end. In ambient environments, the optical probe can be a conventional optical fiber; in elevated temperature environments (e.g., T≧200° C.), such as a combustion environment or a burning cigarette, the optical probe can be a quartz optical fiber. An example of a suitable optical probe has a concentric 6-around-1 configuration (e.g., a multiple optical fiber probe). Due to the high temperatures anticipated in the vapor phase PAH environment, 600-$\mu$m $SiO_2/SiO_2$ fibers were coated with polyimide (e.g., polyimide available from Polymicro Technologies, LLC, Pheonix Ariz.), arranged in a concentric 6-around-1 configuration and bound together with wires. In embodiments utilizing a single optical probe with a multiple fiber arrangement, the center fiber is preferably the excitation fiber in optical communication with the laser, and the surrounding fibers, in optical communication with the wavelength separator, collect the emitted radiation. In embodiments utilizing a plurality of optical probes, combinations of single fiber and multiple fiber optical probes can be used.

Referring to FIG. 1, a positioner 118 can be coupled to the optical path 108 for positioning the distal end 120 of the optical probe 122 at a desired location with respect to the vapor sample produced by source 112. For example, the positioner 118 can be mechanically coupled to the optical path and can slidably position the distal end 120 of the optical probe 122 to be co-located with the area of the material undergoing combustion 124 as the area undergoing combustion of the sample 112 retreats along the length of the sample 112 (e.g., the positioner can move the distal end 120 as combustion of a burning cigarette progresses along the length thereof from distal end 126 toward proximal end 128). Although described as mechanically coupled, the positioner can be coupled by any other arrangements utilizing electromagnetic, piezoelectric, magnetic, or other forces to effect movement of the optical probe.

One advantage of the apparatus according to the invention is that the positioner 118 can relocate the distal end 120 of the optical probe 122 in real time in response to any movement of the area undergoing combustion. For example, the distal end 120 of the optical probe 122 can be continuously positioned in response to a predetermined burning rate of the source 112 (e.g., a burning cigarette can be arranged with a vacuum applied to the filter end so as to draw air through the burning cigarette at a predetermined air flow rate). Alternatively, the distal end 120 of the optical probe 122 can be step-wise relocated by the positioner 118 in accordance with a controller program. Further, repositioning may be responsive to a monitored signal, such as temperature or change in temperature in the area in which the distal end 120 of the optical probe 122 is located or responsive to a visual indication using, for example, thermal imaging to detect an area undergoing combustion and to reposition the distal end 120 of the optical probe 122 accordingly. The distal end 120 of the optical probe 122 can have a calibrated position or can be detected by a sensor which provides information to a control device programmed to control operation of the positioner 118. Additionally, although described herein with reference to the single optical probe 180° backscattered configuration, in embodiments utilizing more than one optical probe in the optical path, the positioner 118 or a plurality of positioners can relocate the optical probes in unison or independently to suitably position the optical probes.

A method is provided in which an optical path capable of withstanding temperatures of a combustion environment can be optically coupled to an excitation source and a wavelength separator, such as a spectrometer, to monitor fluorescence spectra emissions from a vapor sample produced by the combustion environment. Such measurements of vapor samples, specifically of target constituents such as of vapor phase PAHs, can be useful in fluorescence studies, such as in atmospheric environmental monitoring and combustion diagnostics. In one aspect, an optical path can be inserted in an area of a material undergoing combustion and that is emitting combustion gases for optical probing of the combustion environment. As depicted in FIG. 1, the environment that is optically probed can be a burning cigarette. Alternatively, the environment can be an area undergoing combustion of a cigarette-like material, an exhaust gas environment such as exhaust from a combustion engine or a gas turbine engine, effluent at elevated temperatures such as emissions from power generating plants, or other suitable applications.

In situ analysis of combustion environments can be desirable in many respects. For example, the availability of a high-temperature fluorescence emission probe can be used to investigate the method and formation of PAHs in a high-temperature area or an area undergoing combustion of a cigarette. The in situ analysis in such an environment is difficult because oxygen can destroy the PAHs at such high temperatures and/or the lifetime of PAHs at temperatures on the order of approximately 500° C. may be short. However, because of the co-location of the optical probe and the sample area in the present invention, fluorescence emission can be received from a position close to the combustion environment and the time between PAHs generation and interaction with the incident wavelength causing fluorescence can be reduced. The optical probe is preferably positioned sufficiently close to the combustion environment, to enable the detection of fluorescence emitted by a PAH within the PAH lifetime, which can be several milliseconds to several microseconds. Further, by taking a continuous measurement of the cigarette at a particular location from before combustion through the combusting event, both the time and the location of the formation of the PAH can be detected.

PAHs can condense with the aerosol products of combustion, thereby complicating detection and identification of individual PAHs in the aerosol. Accordingly, as an alternative to in situ monitoring, the PAH monitoring apparatus can monitor a PAH in the vapor phase formed from sufficiently elevating the temperature of an aerosol of the combustion products of a cigarette. This environment would be analogous to monitoring the mainstream smoke or sidestream smoke given off from a burning cigarette or "cigarette-like" material when the mainstream smoke or sidestream smoke is at a temperature sufficiently high for PAHs to be in the vapor phase (e.g., prior to condensing to an aerosol). When sampling PAH after condensing to an aerosol, the temperature of the PAH aerosol is first sufficiently elevated (e.g., to between 200° C. and 400° C.) to form vaporized PAH. In this temperature range, the PAH vaporizes and the PAH vapor can be analyzed by any of the previously described embodiments of the PAH monitoring apparatus. For example, the temperature of the PAH aerosol can be sufficiently elevated while the PAH is in a closed container or is flowed through a conduit both of which are equipped with an optical window through which the optical path of the PAH monitoring apparatus is directed.

One of the difficulties associated with monitoring PAHs at high temperatures is the effect of those temperatures on the statistical distribution of various energy levels of the molecule of interest. Increased temperature causes molecules to occupy higher energy levels than are present at ambient temperatures. This feature applies to both the ground state and the excited states of the molecule. Variations in energy level distributions can cause shifts in both the absorption and fluorescence spectra of the molecule. In addition to spectral shifts, spectral broadening effects (e.g. Doppler and pressure linewidth broadening) can also occur at elevated temperatures. The spectral changes of particular PAHs have been identified and further details of fluorescence measurements on polycyclic aromatic hydrocarbons at elevated temperatures can be found in Zhenhuan Chi et al., *Laser-induced Fluorescence Studies of Polycyclic Aromatic Hydrocarbons (PAH) Vapors at High Temperatures*, Spectrochimica Acta Part A, Vol. 57, p. 1377–1384 (2001), the entire contents of which are herein incorporated by reference.

In addition to the spectral characterization of PAHs which may be present in burning cigarettes and "cigarette-like" materials, time-resolved fluorescence measurements (fluorescence lifetime measurements) can be used for species identification. When a chemical species emits fluorescence, the fluorescence emission persists for a certain amount of time following excitation, depending on the spectrochemical properties of the species as well as its local environment. The time it takes for the intensity of this fluorescent light to reach a point that is 1/e as intense as the original fluorescence is termed the fluorescence lifetime of the species. This fluorescence lifetime is very specific to the chemical species of interest and can be used as a means for identifying chemical species either alone or in conjunction with spectral characterization.

The thermal activation energy at high temperatures that affects lower-level vibrational levels (100–2000 $cm^{-1}$) is not expected to significantly affect the electronic levels of PAH, which occur at higher energies (20,000–50,000 $cm^{-1}$) Incandescence emissions due to thermal energy in the area undergoing combustion of a cigarette occurs mainly in the near-infrared and infrared spectral range, whereas the fluorescence of PAHs occurs in the visible range. However, to eliminate such interference from background incandescence signals in the area of a cigarette undergoing combustion, any suitable sensing technique based on time-resolved detection can be utilized to improve accuracy of measurements of the apparatus according to the invention.

In accordance with the invention, fluorescence decay can be monitored using a secondary single optical fiber probe and gating the signal appropriately to acquire fluorescence intensity vs. time. A Fourier transform can be used to change the time domain to frequency domain. The contribution to the data from the laser pulse width can be discarded and the data converted back to fluorescence intensity vs. time. Finally, the data can be interpreted with an exponential series model to calculate the lifetime.

Figure 5:
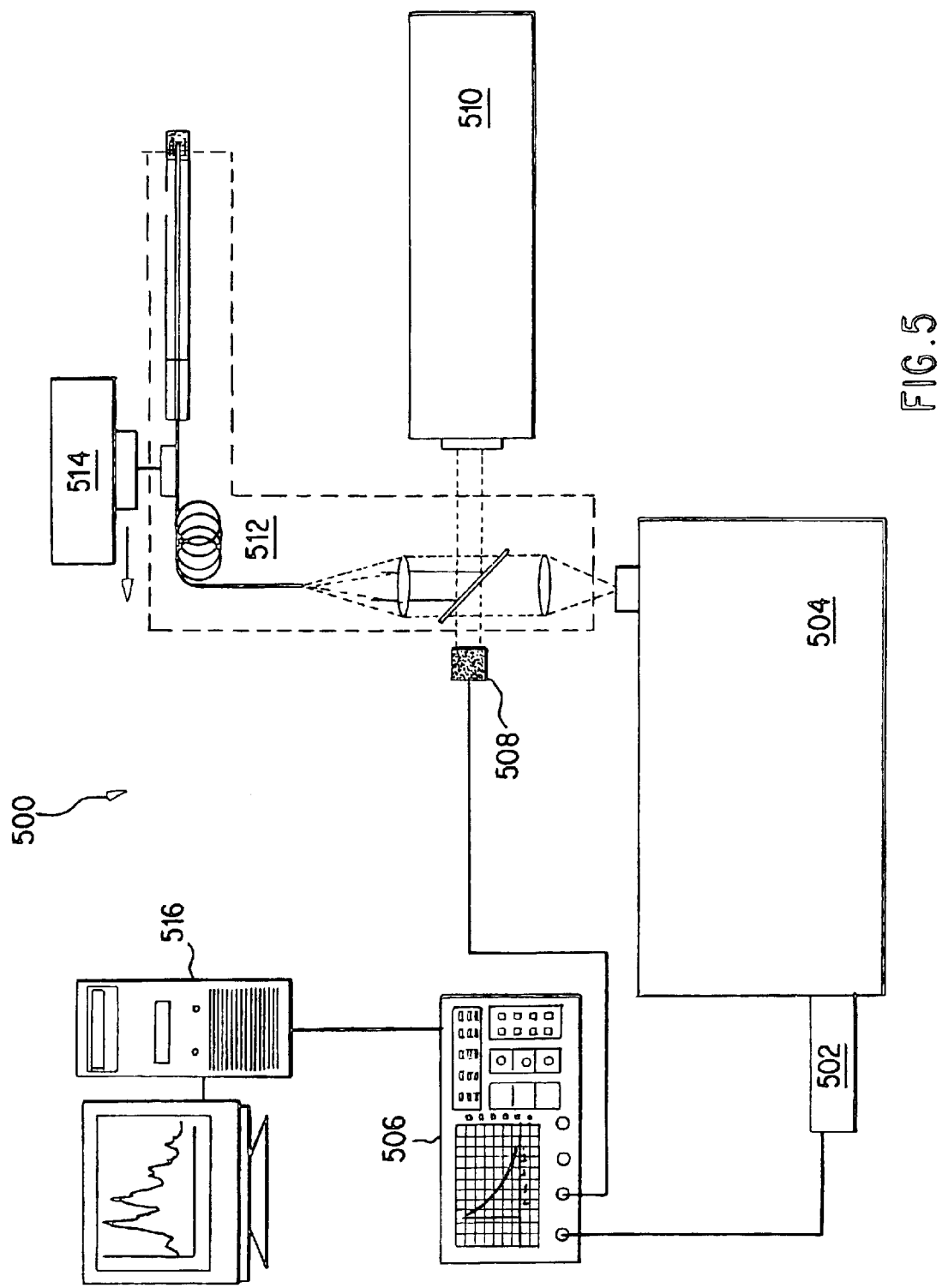
FIG. 5 is an embodiment of a PAH monitoring apparatus for detecting fluorescence lifetime.

For fluorescence lifetime measurements, any apparatus for detecting PAH having a suitable wavelength separator and detector can be used. FIG. 5 is an embodiment of a PAH monitoring apparatus 500 configured to detect fluorescence and determine fluorescence lifetime. The detector 502 is a photomultiplier tube connected to a wavelength separator 504, such as monochromator, the output of which is directly connected to a trigger system, such as fast digital oscilloscope 506 triggered by a photodiode 508 monitoring the laser firing event. This arrangement can be in place of the CCD/spectrometer system previously described in the FIGS. 1–4 embodiments. An example of a suitable photomultiplier tube is Model PR1401RF available from Products for Research, Inc. of Danvers, Mass. The remaining components of the apparatus 500 can be those previously described or equivalents thereof including an excitation source 510 with a laser and/or a pump laser and a dye laser, an optical path 512, and a positioner 514. The oscilloscope 506 can output a signal to a computer 516 for spectrum and lifetime data analysis. The optical path can incorporate a single optical probe 180° backscattered configuration, a dual optical probe 180° backscattered configuration, or a dual optical probe 90° side scattered configuration. Because the data collection in this embodiment is a photomultiplier tube and not a CCD detector, the data collection and the excitation source do not have to be coordinated by a controller.

In an additional example, in any one of the embodiments presented, the use of pulsed laser excitation (e.g., 5 nsec pulse-width, 100 Hz) combined with gated detection (e.g., 10–20 nsec gate) can be used to detect vapor phase PAH fluorescence emissions with lifetimes in the nanosecond range. Referring to the FIG. 1 embodiment, the controller 110 can optionally be equipped with a trigger system 132 operatively interfaced with the components of the apparatus 100 and that can be used to activate the excitation source 102 and send a signal that controls the delay and gating period of the detector 106. In FIG. 1, the trigger system 132 is a unitary instrument. Alternatively, the trigger system 132 can be an individual trigger instrument and a timing controller operatively interfaced with the components of the apparatus 100. Although the use of a trigger system 132 has been illustrated only with respect to the embodiment of a monitoring apparatus as shown in FIG. 1, a trigger system can similarly be used in any embodiment of the monitoring system to provide time-resolved detection capability.

In an example of measuring fluorescence lifetime according to the invention, a fluorescence decay curve is measured and recorded on an oscilloscope following the excitation laser pulse. The decay cure is then deconvoluted by a common Fourier domain deconvolution process, such as that described in J. C. Andre et al., *J. Phys. Chem.*, vol. 83, p. 2285 (1979), and the fluorescence lifetime calculated.

Conventional quantitative analysis of fluorescence spectra utilizes peak height measurements of fluorescence bands. However, in both the standard measurement and the lifetime measurement, the second derivative of the spectra can also be used to identify the specific PAH. The second derivative method improves the identification of the components in the complex PAH spectrum by locating the fluorescence maxima and spectral shoulders, and aiding in the characterization of the complex PAH samples.

An additional measuring technique according to the invention, uses chemometrics methodology to identify unknown species in complex mixtures based on partial least squares (PLS) regression. The chemometrics methodology can be used in various applications, such as Raman spectra of chemical species as well as fluorescence spectra of multi-component PAH mixtures. Chemometrics is a powerful analysis tool that can be used to statistically correlate spectral variations to spectrochemical properties. A fluorescence spectral database of PAHs can be established to model multi-component fluorescence spectra. By combining chemometrics and computing, a PAH can be identified from complex spectra of burning materials.

Figure 6:
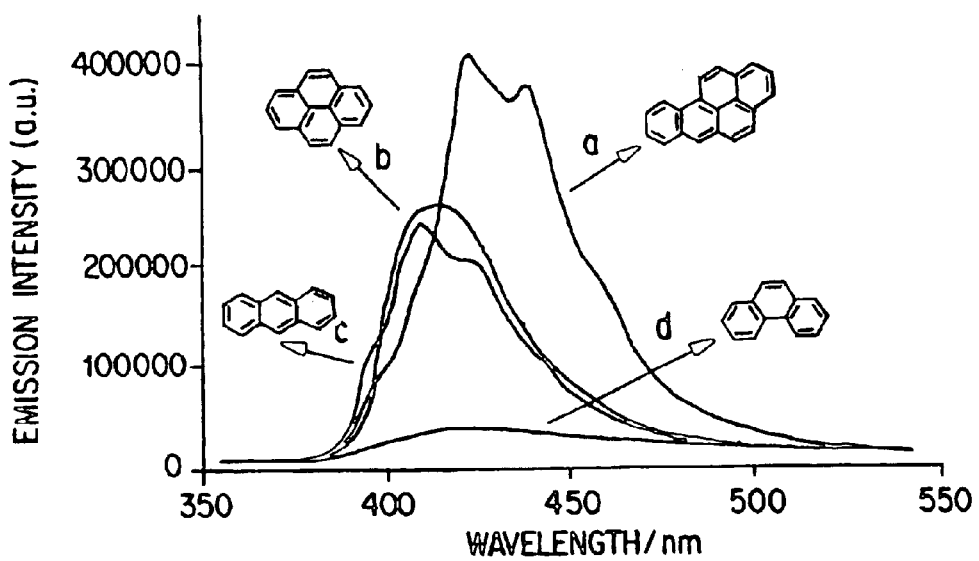
FIG. 6 shows spectra from (a) benzo[a]pyrene, (b) pyrene, (c) anthracene, and (d) phenanthrene collected by a PAH monitoring apparatus.
Figure 7:
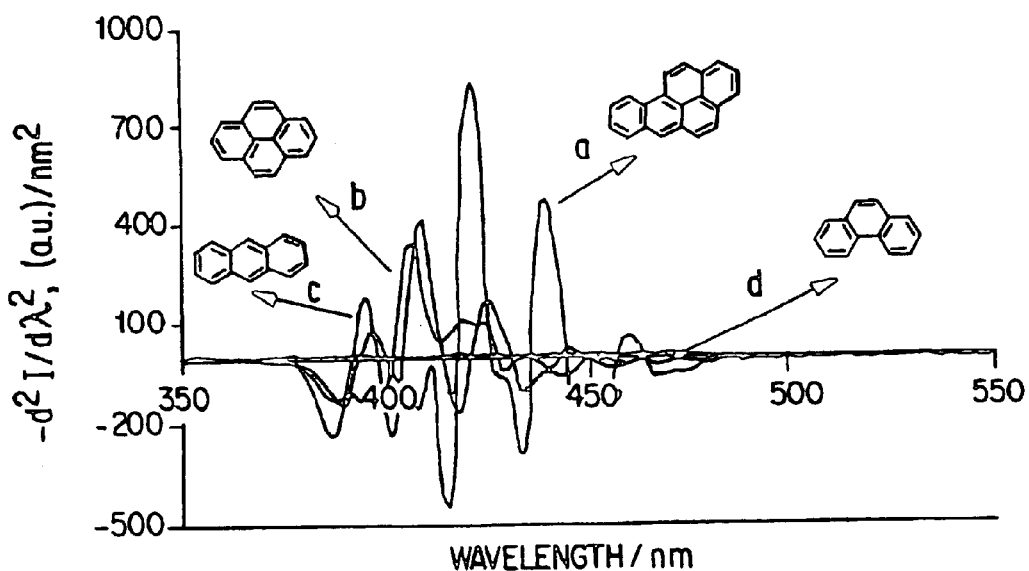
FIG. 7 shows the second derivative of the four spectra of FIG. 6.

In a further measuring technique according to the invention, a database of PAH spectra can be created from standards of PAH containing samples and the database can be accessed and compared to collected spectra, as by, for example, a computer. As an example, spectra from four PAH compounds (e.g., benzo(a)pyrene, pyrene, anthracene, and phenanthrene) were collected by the PAH monitoring apparatus according to the invention. FIG. 6 and FIG. 7 show the spectra and second derivative of the spectra, respectively, and in which (a) is benzo(a)pyrene, (b) is pyrene, (c) is anthracene, and (d) is phenanthrene.

Although the present invention has been described in connection with exemplary embodiments thereof, it will be appreciated by those skilled in the art that additions, deletions, modifications, and substitutions not specifically described may be made without departing from the spirit and scope of the invention as defined in the appended claims.

What is claimed is:

1. A monitoring apparatus for one or more vapor phase polycyclic aromatic hydrocarbons in a high-temperature environment of a burning cigarette, comprising:

an excitation source producing electromagnetic radiation;

an optical path having at least a first optical probe, the optical path optically communicating the electromagnetic radiation received at a proximal end of the first optical probe to a distal end thereof such that the electromagnetic radiation interacts with at least one vapor phase polycyclic aromatic hydrocarbon produced by a material of the burning cigarette undergoing combustion and produces at least one emitted wavelength of radiation characteristic of the at least one vapor phase polycyclic aromatic hydrocarbon; and a positioner coupled to the first optical path, wherein the positioner slidably moves the distal end of at least the first optical probe to maintain the distal end position at a desired position with respect to an area of the material of the burning cigarette undergoing combustion.

2. The monitoring apparatus of claim 1, further comprising:

a wavelength separator in optical communication with the first optical probe to receive the at least one emitted wavelength of radiation; and a detector operatively connected to the wavelength separator, wherein the first optical probe receives the at least one emitted wavelength of radiation at the distal end and optically communicates the at least one emitted wavelength of from the distal end of the first optical probe to the proximal end thereof such that the at least one emitted wavelength of radiation is received by the wavelength separator.

3. The monitoring apparatus of claim 2, further comprising a trigger system, the trigger system operatively communicating with the excitation source and the detector.

4. The monitoring apparatus of claim 2, wherein the wavelength separator comprises a spectrometer.

5. The monitoring apparatus of claim 2, wherein the wavelength separator comprises a monochromator or a polychromator.

6. The monitoring apparatus of claim 2, wherein the detector is a CCD camera, a photodiode array, or a photomultiplier tube.

7. The monitoring apparatus of claim 1, wherein the positioner is coupled mechanically, electromagnetically, magnetically, or piezoelectrically to the first optical path.

8. The monitoring apparatus of claim 1, wherein the first optical probe is arranged in a 180° backscatter geometry.

9. The monitoring apparatus of claim 1, further comprising:

a second optical probe, wherein the second optical probe optically receives the at least one emitted wavelength of radiation emitted from the vapor phase polycyclic aromatic hydrocarbon and directs the at least one emitted wavelength of radiation to a wavelength separator.

10. The monitoring apparatus of claim 9, wherein the first optical probe and second optical probe are arranged in a 180° backscatter geometry, a 90° side scatter geometry or at an angle θ from 0 to 180°.

11. The monitoring apparatus of claim 9, wherein the second optical probe is slidably movable such that a distal end of the second optical probe is maintained at a desired position with respect to an area of the material undergoing combustion.

12. The monitoring apparatus of claim 1, wherein the first optical probe includes a plurality of optical fibers.

13. The monitoring apparatus of claim 1, wherein the excitation source comprises a laser.

14. The monitoring apparatus of claim 13, wherein the excitation source further comprises a dye module.

15. The monitoring apparatus of claim 13, wherein the excitation source further comprises an all solid-state tunable source.

16. The monitoring apparatus of claim 1, wherein the excitation source is a nitrogen laser.

17. The monitoring apparatus of claim 16, further comprising:

a photodiode in optical communication with the excitation source; and a data collecting device in operative communication with the detector.

18. A monitoring apparatus for one or more vapor phase polycyclic aromatic hydrocarbons in a high-temperature environment, comprising:

an excitation source producing electromagnetic radiation;

an optical path having at least a first optical probe, the optical path optically communicating the electromagnetic radiation received at a proximal end of the first optical probe to a distal end thereof such that the electromagnetic radiation interacts with at least one vapor phase polycyclic aromatic hydrocarbon produced by a material undergoing combustion and produces at least one emitted wavelength of radiation characteristic of the at least one vapor phase polycyclic aromatic hydrocarbon; and a positioner coupled to the first optical path, wherein the positioner slidably moves the distal end of at least the first optical probe to maintain the distal end position at a desired position with respect to an area of the material undergoing combustion, wherein the first optical probe comprises a plurality of 600-$\mu$m SiO$_2$/SiO$_2$ fibers, at least one of the fibers being coated at the distal end thereof with a polyimide.

19. The monitoring apparatus of claim 18, wherein the plurality of fibers are arranged in a concentric 6-around-1 configuration.

20. A monitoring apparatus for one or more vapor phase polycyclic aromatic hydrocarbons in a high-temperature environment, comprising:

an excitation source producing electromagnetic radiation;

an optical path having at least a first optical probe, the optical path optically communicating the electromagnetic radiation received at a proximal end of the first optical probe to a distal end thereof such that the electromagnetic radiation interacts with at least one vapor phase polycyclic aromatic hydrocarbon produced by a material undergoing combustion and produces at least one emitted wavelength of radiation characteristic of the at least one vapor phase polycyclic aromatic hydrocarbon; and a positioner coupled to the first optical path, wherein the positioner slidably moves the distal end of at least the first optical probe to maintain the distal end position at a desired position with respect to an area of the material undergoing combustion, wherein the excitation source further comprises an all solid-state tunable source is equipped with an optical parametric oscillator.

21. A monitoring apparatus for one or more vapor phase polycyclic aromatic hydrocarbons in a high-temperature environment, comprising:

an excitation source producing electromagnetic radiation;

an optical path having at least a first optical probe, the optical path optically communicating the electromagnetic radiation received at a proximal end of the first optical probe to a distal end thereof such that the electromagnetic radiation interacts with at least one vapor phase polycyclic aromatic hydrocarbon produced by a material undergoing combustion and produces at least one emitted wavelength of radiation characteristic of the at least one vapor phase polycyclic aromatic hydrocarbon;

a positioner coupled to the first optical path, wherein the positioner slidably moves the distal end of at least the first optical probe to maintain the distal end position at a desired position with respect to an area of the material undergoing combustion;

a photodiode in optical communication with the excitation source; and a data collecting device in operative communication with the detector, wherein the data collecting device comprises an oscilloscope and the excitation source is a nitrogen laser.

22. A vapor phase polycyclic aromatic hydrocarbon monitoring apparatus, comprising:

means for generating electromagnetic radiation;

means for directing the electromagnetic radiation to a gaseous by-product produced by a material of a cigarette undergoing combustion; and means for receiving emitted radiation from the material of the cigarette undergoing combustion having at least one wavelength characteristic of at least one polycyclic aromatic hydrocarbon and directing the emitted radiation to a detecting means, wherein the means for receiving the emitted radiation is positionable to be co-located with the material of the cigarette undergoing combustion such that the emitted radiation is collected.

23. The monitoring apparatus of claim 22, further comprising means for analyzing the emitted radiation from the material undergoing combustion.

24. The monitoring apparatus of claim 22, further comprising means for time resolving the monitoring apparatus.

25. The monitoring apparatus of claim 22, wherein the means for directing the electromagnetic radiation comprises an optical probe positioned within the material of the cigarette undergoing combustion.

26. The monitoring apparatus of claim 25, wherein the material of the cigarette undergoing combustion is a cellulosic material, a cut filler, or a combination thereof.

27. A vapor phase polycyclic aromatic hydrocarbon monitoring apparatus, comprising:

means for generating electromagnetic radiation;

means for directing the electromagnetic radiation to a gaseous by-product produced by a material undergoing combustion; and means for receiving emitted radiation from the material undergoing combustion having at least one wavelength characteristic of at least one polycyclic aromatic hydrocarbon and directing the emitted radiation to a detecting means, wherein the means for directing the electromagnetic radiation is positionable to be co-located with the material undergoing combustion such that the electromagnetic radiation causes emitted radiation from the material undergoing combustion and the means for receiving the emitted radiation is positionable to be co-located with the material undergoing combustion such that the emitted radiation is collected, wherein the means for directing the electromagnetic radiation comprises an optical probe positioned within a burning cigarette.

28. A method of monitoring at least one vapor phase polycyclic aromatic hydrocarbon using electromagnetic radiation, comprising:

producing electromagnetic radiation;

directing the electromagnetic radiation along a first optical probe;

positioning a distal end of the first optical probe with respect to an area containing gaseous by-products produced by combustion of a cigarette;

interacting at least a portion of the produced electromagnetic radiation with the gaseous by-products to produce emitted radiation characteristic of at least one polycyclic aromatic hydrocarbon; and monitoring the emitted radiation.

29. The method of claim 28, wherein the monitoring comprises directing the emitted radiation to a wavelength separator using the first optical probe.

30. The method of claim 28, wherein the monitoring comprises directing the emitted radiation to a wavelength separator using a second optical probe.

31. The method of claim 28, wherein the electromagnetic radiation is produced from an excitation source.

32. The method of claim 28, wherein the positioning is carried out using mechanical, magnetic, electromagnetic or piezoelectric energy to dynamically position the distal end of the first optical probe.

33. The method of claim 28, wherein at least a portion of the electromagnetic radiation has a wavelength of energy that excites an electron of a vapor phase polycyclic aromatic hydrocarbon to an excited state from which the electron returns to a lower energy state with a concomitant generation of a characteristic emitted wavelength.

34. The method of claim 28, wherein the electromagnetic radiation is a wavelength of energy at approximately 337 nm.

35. The method of claim 28, further comprising detecting a vapor phase polycyclic aromatic hydrocarbon by a characteristic wavelength contained in the emitted radiation.

36. The method of claim 28, wherein the step of positioning locates the distal end of the first optical probe substantially co-located outside the cigarette, within a combustion zone of the cigarette, or within an area of the cigarette outside the combustion zone.

37. The method of claim 36, further comprising gating a fluorescence signal in response to the electromagnetic radiation incident on a photodiode to detect a fluorescence intensity as a function of time, thereby time resolving the detecting step.

38. A method of monitoring at least one vapor phase polycyclic aromatic hydrocarbon using electromagnetic radiation, comprising:

producing electromagnetic radiation;

directing the electromagnetic radiation along a first optical probe;

positioning a distal end of the first optical probe with respect to an area containing gaseous by-products of a material undergoing combustion;

interacting at least a portion of the produced electromagnetic radiation with the gaseous by-products to produce emitted radiation characteristic of at least one polycyclic aromatic hydrocarbon; and monitoring the emitted radiation, wherein the material undergoing combustion is a cigarette, a cigarette-like sample, or a fuel.

39. A method of monitoring at least one vapor phase polycyclic aromatic hydrocarbon using electromagnetic radiation, comprising:

producing electromagnetic radiation;

directing the electromagnetic radiation along a first optical probe;

positioning a distal end of the first optical probe with respect to an area containing gaseous by-products of a material undergoing combustion;

interacting at least a portion of the produced electromagnetic radiation with the gaseous by-products to produce emitted radiation characteristic of at least one polycyclic aromatic hydrocarbon; and monitoring the emitted radiation, wherein the material undergoing combustion is an aerosol sample of mainstream smoke or sidestream smoke from the combustion of a cigarette or a cigarette-like material.

* * * * *